United States Patent [19]

Decker et al.

[11] Patent Number: 4,895,985
[45] Date of Patent: Jan. 23, 1990

[54] PREPARATION OF CYCLOPENTANONE

[75] Inventors: Martin Decker, Ludwigshafen; Harro Wache, Fussogoenheim; Wolfgang Franzischka, Frankenthal, all of Fed. Rep. of Germany

[73] Assignee: BASF Aktiengesellschaft, Ludwigshafen, Fed. Rep. of Germany

[21] Appl. No.: 236,210

[22] Filed: Aug. 25, 1988

[30] Foreign Application Priority Data

Sep. 9, 1987 [DE] Fed. Rep. of Germany ....... 3730185

[51] Int. Cl.$^4$ ............................................. C07C 45/45
[52] U.S. Cl. ...................................................... 568/355
[58] Field of Search ........................................ 568/355

[56] References Cited

U.S. PATENT DOCUMENTS

| | | | |
|---|---|---|---|
| 1,702,844 | 2/1929 | Ruzicka | 568/355 |
| 2,612,524 | 9/1950 | Zettlemoyer et al. | 568/355 |
| 4,788,353 | 11/1988 | Kleine-Homann | 568/355 |

FOREIGN PATENT DOCUMENTS

| | | | |
|---|---|---|---|
| 0251111 | 1/1988 | European Pat. Off. | 568/355 |
| 0266687 | 1/1988 | European Pat. Off. | 568/355 |
| 256622 | 12/1911 | Fed. Rep. of Germany | 568/355 |
| 743967 | 11/1943 | Fed. Rep. of Germany | 568/355 |

OTHER PUBLICATIONS

Chem. Abstr., vol. 98; 47408f.
Chem. Abstr., vol. 98; 34199k.

*Primary Examiner*—James H. Reamer
*Attorney, Agent, or Firm*—Keil & Weinkauf

[57] ABSTRACT

The invention relates to a process for the preparation of cyclopentanone from adipic acid wherein adipic acid vapor in an inert gas at a temperature of from 250° C. to 450° C., possibly accompanied by water vapor, is passed over an oxygenous acidic or basic catalyst.

6 Claims, No Drawings

PREPARATION OF CYCLOPENTANONE

The present invention relates to the process described in the claims.

The preparation of cyclopentanone from adipic acid is known. The conversion of molten adipic acid to cyclopentanone in the presence of metal oxides or powdered metals is described in DE-A 256 522. One great problem about this kind of process is the corrosive action of the reaction mixture, and in addition linear polyoxodicarboxylic acids are formed as well as cyclic ketones, as reported in, for example, Chem. Abstr., 80, 47408f (1974) and Chem. Abstr., 98, 34199k (1983).

When adiponitrile is prepared by the reaction of adipic acid with ammonia small proportions of cyclopentanone are formed, and the impure compound can be isolated from the first runnings of the adiponitrile distillation (see DE-A 743 967). It is however difficult to purify the product.

The disadvantages mentioned are avoided by the novel process, which gives high yields of very pure cyclopentanone. The acidic or basic oxygenous catalysts used to promote the decomposition of the dicarboxylic acid are employed to advantage as fine particles in a fluidized bed and the dicarboxylic acid is introduced into the heated bed as a powder suspended in an inert gas, preferably nitrogen.

Suitable catalysts are, for instance, alumina or silica of particle size between 0.05 mm and 0.3 mm carrying catalytically active substances. Suitable active substances for application to silica include phosphoric acid and sodium dihydrogen phosphate. The catalyst may contain, for instance, up to 10% of the phosphorus compound, and can be prepared by mixing silica gel and the phosphate salt and spraying, drying, and calcining the mixture. Cyclopentanone is obtained in high yield and purity when this catalyst is employed in the novel process.

The basic catalysts contain to advantage one or more oxides of metals of subgroups
1A and
2A of the periodic table on a support such as alumina. When they are used the yield and purity of the cyclopentanone is improved when water vapor is introduced into the gas stream: from 2 mol to 10 mol—preferably from 4 mol to 6 mol—of water per mole of dicarboxylic acid. It is not necessary to introduce water when acidic catalysts are used.

The decomposition of the dicarboxylic acids takes place in the gaseous phase at temperatures of from 200° C. to 450° C., preferably from 300° C. to 400° C. The lower part of the temperature range is preferred when basic catalysts are used, the upper part when acidic catalysts are used. Generally the reaction is carried out under atmospheric pressure or slightly increased pressures of up to about 2 bar, but it is possible to carry it out under reduced pressure, which can be advantageous because the dicarboxylic acid then volatilizes more easily.

Particular advantages of the novel process are the avoidance of corrosion of the production plant and the high yield and purity of the product. Cyclopentanone is a valuable intermediate that is used mainly for the syntheses of biologically active compounds.

EXAMPLE 1

A fluidized-bed reactor 60 mm in diameter is packed with 335 g of catalyst of particle size from 0.06 mm to 0.30 mm consisting of a mixture of 90% silica and 10% sodium dihydrogen phosphate.

Nitrogen at a temperature of 360° C. is introduced into the reactor through a distributor at the bottom at a rate equivalent to 200 l/h at s.t.p. and fluidizes the catalyst. Water injected into the nitrogen stream at the rate of 163 g/h passes through the catalyst bed as vapor.

Solid adipic acid suspended in a stream of nitrogen at a temperature of about 20° C. flowing at the rate of 200 l/h is introduced through a side tube just above the gas distributor at the rate of 200 g/h. The temperature of the catalyst bed is maintained at 400° C. by means of electrical heating. The gaseous mixture leaving the reactor passes through a filter and is then cooled and scrubbed in a tower through which methanol is pumped.

A total of 1810 g of adipic acid employed gives 3083 g of a mixture containing 909.3 g of cyclopentanone, a yield of 87.3%.

EXAMPLE 2

Adipic acid is introduced into the reactor at the rate of 214 g/h as described in Example 1, but no water is injected into the nitrogen stream as it is heated. The reaction conditions and treatment of the reaction products are otherwise as described in Example 1.

A total of 2570 g of adipic acid introduced into the reactor gives 2593 g of a solution of the reaction products in methanol containing 1307.1 g of cyclopentanone, a yield of 88.4%.

EXAMPLE 3

Alumina of particle size from 0.05 mm to 0.30 mm is impregnated with barium acetate solution so that the catalyst obtained by drying and heating at 500° C. contains 5% of barium oxide. The fluidized-bed reactor described in Example 1 is packed with 750 ml of this catalyst.

In the way described in Example 1 adipic acid is introduced at the rate of 201 g/h into the reactor, which is maintained at a temperature of 345° C. Water is injected at the rate of 149 g/h into the nitrogen stream, which is heated to a temperature of 300° C. and introduced through the distributor into the catalyst bed.

The reaction products are collected as described in Example 1. A total of 1814 g of adipic acid gives 919.3 g of cyclopentanone, a yield of 88.1%.

EXAMPLE 4

Catalyst consisting of 85% of alumina, 5% of barium oxide, 5% of vanadium oxide, and 5% of antimony oxide is used.

Adipic acid is introduced into the catalyst bed at the rate of 146 g/h. Water is injected into the nitrogen stream at various rates. The remaining conditions and the way the reaction products are collected are as in Example 3.

The yield of cyclopentanone varies with the proportion of water vapor added, as shown in the table.

| Reaction temperature/°C. | Amount of substance/mol | | Yield/% |
|---|---|---|---|
| | Adipic acid | Water | |
| 320 | 1 | 2 | 62.6 |

-continued

| Reaction temperature/°C. | Amount of substance/mol | | Yield/% |
|---|---|---|---|
| | Adipic acid | Water | |
| 320 | 1 | 3 | 74.4 |
| 320 | 1 | 6 | 82.7 |

We claim:

1. A process for the preparation of cyclopentanone from adipic acid wherein adipic acid vapor in an inert gas at a temperature of from 250° C. to 450° C., possibly accompanied by water vapor, is passed over an oxygenous acidic catalyst, which comprises silica mixed with phosphoric acid or a hydrogen phosphate or a basic catalyst, which comprises alumina mixed with elements of subgroups 1A or 2A of the periodic table.

2. A process as claimed in claim 1 wherein from 2 mol to 10 mol of water vapor per mole of adipic acid is introduced into the inert gas.

3. A process as claimed in claim 1 wherein from 4 mol to 6 mol of water vapor per mole of adipic acid is introduced into the inert gas.

4. A process as claimed in claim 1 wherein the inert gas is nitrogen.

5. A process as claimed in claim 1 wherein the process is carried out in a fluidized bed.

6. A process as claimed in claim 1 wherein the adipic acid is introduced as the solid into the fluidized bed.

* * * * *